(12) United States Patent
Ali et al.

(10) Patent No.: US 10,473,006 B2
(45) Date of Patent: Nov. 12, 2019

(54) METHOD AND APPARATUS

(71) Applicants: Castrol Limited, Berkshire (GB); Rana Ali, Berkshire (GB); Steven Paul Goodier, Berkshire (GB); Richard Pearson, Berkshire (GB); Oliver Paul Taylor, Berkshire (GB)

(72) Inventors: Rana Ali, Berkshire (GB); Steven Paul Goodier, Berkshire (GB); Richard Pearson, Berkshire (GB); Oliver Paul Taylor, Berkshire (GB)

(73) Assignee: Castrol Limited, Reading (GB)

( * ) Notice: Subject to any disclaimer, the term of this patent is extended or adjusted under 35 U.S.C. 154(b) by 289 days.

(21) Appl. No.: 15/312,556

(22) PCT Filed: May 21, 2015

(86) PCT No.: PCT/EP2015/061334
§ 371 (c)(1),
(2) Date: Nov. 18, 2016

(87) PCT Pub. No.: WO2015/177316
PCT Pub. Date: Nov. 26, 2015

(65) Prior Publication Data
US 2017/0107873 A1      Apr. 20, 2017

(30) Foreign Application Priority Data

May 21, 2014   (GB) .................................. 1409064.1

(51) Int. Cl.
*F01M 1/16*     (2006.01)
*F01M 13/00*    (2006.01)
(Continued)

(52) U.S. Cl.
CPC ............... *F01M 1/16* (2013.01); *F01M 1/02* (2013.01); *F01M 1/12* (2013.01);
(Continued)

(58) Field of Classification Search
CPC .. F01M 13/00; F01M 2013/0083; F01M 1/18; F01M 2013/0038; F01M 13/021; F01M 3/00; F01M 1/04
See application file for complete search history.

(56) References Cited

U.S. PATENT DOCUMENTS

| | | | |
|---|---|---|---|
| 4,151,823 A | 5/1979 | Grosse et al. | |
| 4,856,487 A | 8/1989 | Furuya | |

(Continued)

FOREIGN PATENT DOCUMENTS

| | | |
|---|---|---|
| DE | 100 13 590 | 9/2001 |
| DE | 10153120 | 9/2002 |

(Continued)

*Primary Examiner* — Long T Tran
(74) *Attorney, Agent, or Firm* — McDonnell Boehnen Hulbert & Berghoff LLP

(57) ABSTRACT

In some embodiments, there is provided a method of controlling a pressure gradient between a combustion chamber and a crankcase of an engine, the method having: receiving, at a control device, a signal indicating that a lubricant container is coupled to a lubricant circulation system associated with the engine, in response to the received signal, providing data to cause operation of a suction control device for facilitating control of the pressure gradient.

47 Claims, 6 Drawing Sheets

Figure 1:
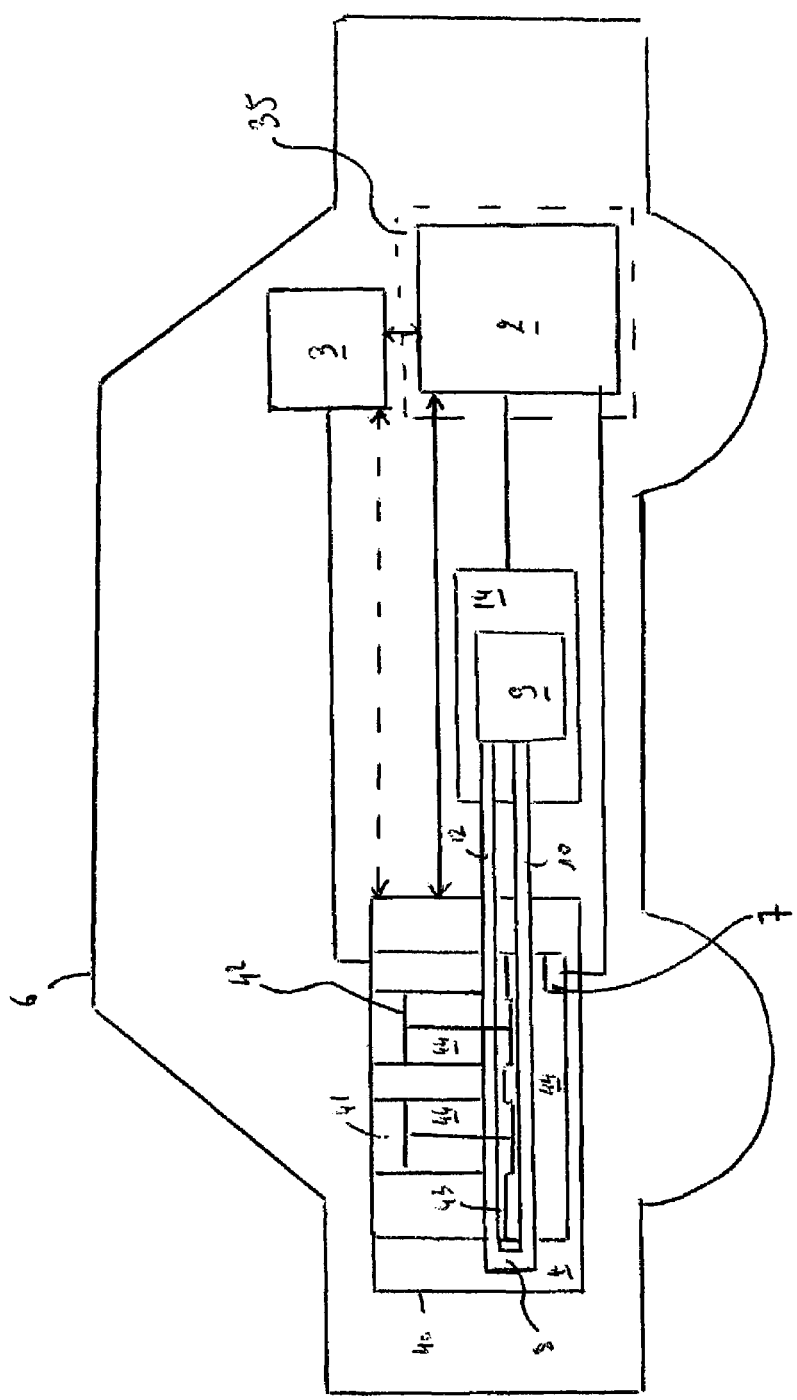

(51) Int. Cl.
  *F01M 1/12*    (2006.01)
  *F01M 11/10*   (2006.01)
  *F01M 1/02*    (2006.01)
  *F01M 11/00*   (2006.01)
  *F01M 13/02*   (2006.01)
  *G01N 33/28*   (2006.01)
  *F01M 11/12*   (2006.01)

(52) U.S. Cl.
  CPC ......... *F01M 11/0004* (2013.01); *F01M 11/10* (2013.01); *F01M 13/021* (2013.01); *G01N 33/28* (2013.01); *F01M 11/12* (2013.01); *F01M 2001/0207* (2013.01); *F01M 2001/126* (2013.01); *F01M 2011/0095* (2013.01); *F01M 2013/0005* (2013.01); *F01M 2013/026* (2013.01); *F16N 2250/00* (2013.01); *F16N 2250/08* (2013.01); *F16N 2250/18* (2013.01); *F16N 2250/36* (2013.01)

(56) References Cited

U.S. PATENT DOCUMENTS

| | | | | |
|---|---|---|---|---|
| 5,027,758 | A * | 7/1991 | Siegler | F01M 3/02 |
| | | | | 123/527 |
| 5,454,354 | A | 10/1995 | Miller | |
| 6,089,213 | A * | 7/2000 | Laudien | F01M 13/04 |
| | | | | 123/572 |
| 6,837,205 | B1 * | 1/2005 | Chipperfield | F16J 9/06 |
| | | | | 123/193.6 |
| 7,490,586 | B1 * | 2/2009 | Weller | F01M 9/02 |
| | | | | 123/196 S |
| 2004/0069286 | A1 * | 4/2004 | Knowles | F01M 13/022 |
| | | | | 123/572 |
| 2004/0112346 | A1 | 6/2004 | Ahlbom et al. | |
| 2006/0102429 | A1 | 5/2006 | Suzuki et al. | |
| 2009/0218169 | A1 | 9/2009 | Kawamura et al. | |
| 2011/0120432 | A1 * | 5/2011 | Ulrey | F02D 9/12 |
| | | | | 123/568.15 |
| 2011/0226203 | A1 * | 9/2011 | Nelander | F02D 13/08 |
| | | | | 123/90.17 |
| 2011/0239965 | A1 | 10/2011 | Ingelfinger et al. | |
| 2011/0253092 | A1 | 10/2011 | Springer et al. | |
| 2012/0204840 | A1 * | 8/2012 | Sugiyama | F02M 5/125 |
| | | | | 123/495 |
| 2013/0291843 | A1 | 11/2013 | Kitayama et al. | |
| 2013/0340732 | A1 | 12/2013 | Pursifull et al. | |
| 2014/0081550 | A1 * | 3/2014 | Jentz | F01M 1/18 |
| | | | | 701/101 |
| 2014/0081564 | A1 | 3/2014 | Pursifull et al. | |
| 2015/0285111 | A1 * | 10/2015 | Rollinger | F01M 13/00 |
| | | | | 123/559.1 |
| 2015/0291317 | A1 | 10/2015 | Brett et al. | |
| 2015/0291318 | A1 | 10/2015 | Barnes et al. | |
| 2015/0292371 | A1 | 10/2015 | Barnes et al. | |
| 2015/0292372 | A1 | 10/2015 | Barnes et al. | |
| 2015/0292674 | A1 | 10/2015 | Brett et al. | |
| 2015/0322895 | A1 * | 11/2015 | Mavinahally | F01M 1/02 |
| | | | | 123/527 |
| 2017/0089234 | A1 | 3/2017 | Dawson et al. | |
| 2017/0089235 | A1 | 3/2017 | Dawson et al. | |
| 2017/0089236 | A1 | 3/2017 | Andersen et al. | |
| 2017/0101911 | A1 | 4/2017 | Barnes et al. | |
| 2017/0122151 | A1 | 5/2017 | Brett et al. | |
| 2017/0183992 | A1 | 6/2017 | Barnes et al. | |
| 2017/0190466 | A1 | 7/2017 | Andersen et al. | |
| 2017/0197596 | A1 | 7/2017 | Barnes et al. | |

FOREIGN PATENT DOCUMENTS

| | | |
|---|---|---|
| DE | 10 2012 011834 | 12/2013 |
| DE | 102012024365 | 6/2014 |
| EP | 2698510 | 2/2014 |
| JP | H06 42325 | 2/1994 |
| JP | H07-317547 | 12/1995 |
| JP | 2002-042969 | 2/2002 |
| JP | 2004-108282 | 4/2004 |
| JP | 2005-036677 | 2/2005 |
| JP | 2006-242160 | 9/2006 |
| JP | 2006-524782 | 11/2006 |
| JP | 2007-198360 | 8/2007 |
| JP | 2008-267273 | 11/2008 |
| JP | 2009-191790 | 8/2009 |
| JP | 2010-038146 | 2/2010 |
| JP | 2010-084534 | 4/2010 |
| JP | 2010-096033 | 4/2010 |
| JP | 2010-163990 | 7/2010 |
| JP | 2010-209843 | 9/2010 |
| JP | 2011-127579 | 6/2011 |
| JP | 2012-137055 | 7/2012 |
| JP | 2013-147949 | 8/2013 |
| JP | 2013-164072 | 8/2013 |
| WO | WO 2012/095953 | 7/2012 |
| WO | WO 2012/140734 | 10/2012 |
| WO | WO 2016/158971 | 10/2016 |

\* cited by examiner

METHOD AND APPARATUS

CROSS REFERENCE TO RELATED APPLICATIONS

The present application is a National Phase application of, and claims the benefit of, International (PCT) Application No. PCT/EP2015/061334, filed on May 21, 2015, which claims priority to GB Application No. 1409064.1, filed on May 21, 2014, the entire contents of both which are incorporated herein by reference.

This invention relates to a method and apparatus, in particular but not exclusively for an internal combustion engine.

Many vehicles use internal combustion engines where a mixture of air and fuel may be ignited by spark plugs, in a combustion chamber provided in a cylinder of the engine.

The combustion of the mixture causes movement of a piston in the cylinder. The pistons of the engine are coupled via connecting rods to a crankshaft housed in a crankcase of the engine for driving wheels of the vehicle.

It is desirable to launch on the market smaller engines with high specific torque (i.e. torque per unit engine swept volume) and high power output, operating at low maximum rotational speeds e.g., around 5000 revs/min (revolutions/minute).

However such engines are usually pressure-charged and are prone to abnormal combustion events such as pre-ignition, which occurs when the air and fuel mixture ignites before the intended ignition by the spark of the spark plugs. Pre-ignition may lead to mega-knock (sometimes referred to as "super-knock").

Mega-knock is undesirable as it may provoke damage to the pistons, connecting rod, spark plug, or other parts of the engine by excessive mechanical loading from very high cylinder pressures.

There may be several causes to pre-ignition which can lead to mega-knock. The causes of pre-ignition include the presence, in the combustion chamber, of lubricant otherwise intended to lubricate the bearings and parts—such as a cylinder liner and crankshaft—of the engine and usually collected in a sump of the crankcase. Lubricant can accumulate in the region around a top piston ring and the liner, and can be ejected into the combustion chamber where its temperature may subsequently cause a pre-ignition event.

Aspects of the disclosure address or at least ameliorate at least one of the above issues.

In an aspect of the present disclosure, there is provided a method of controlling a pressure gradient between a combustion chamber and a crankcase of an engine, the method comprising:
 receiving, at a control device, a signal indicating that a lubricant container is coupled to a lubricant circulation system associated with the engine,
 in response to the received signal, providing data to cause operation of a suction control device for facilitating control of the pressure gradient.

Controlling and/or maintaining a pressure gradient between a combustion chamber and a crankcase of an engine enables inhibiting or reducing entry of lubricant from the crankcase into the combustion chamber, thus allowing mitigation of abnormal combustion events such as pre-ignition in the combustion chamber of the engine. A lower pressure in the crankcase of the engine compared to the pressure in the combustion chamber of the engine inhibits or reduces infiltration of the lubricant in the combustion chamber through a space between the piston and a corresponding liner of the cylinder of the engine. A lower pressure in the crankcase of the engine compared to the pressure in the combustion chamber of the engine reduces the propensity for lubricant to accumulate around the top of the piston ring and the liner, thus inhibiting or reducing the tendency of the lubricant to enter the combustion chamber, and therefore inhibiting or reducing the abnormal combustion events such as pre-ignition events, for example by minimizing a frequency of pre-ignition events.

The suction control device may comprise at least an element selected from a list comprising: a pump, a throttle, an orifice, and/or a venturi effect system.

The method may further comprise sensing at least one property of the crankcase of the engine, and the provided data may be based on the sensed property. The property of the crankcase may be at least one property selected from the group consisting of: a pressure in the crankcase, a temperature in the crankcase, an amount of lubricant in the crankcase, a viscosity of the lubricant in the crankcase, a density of the lubricant in the crankcase, and/or a chemical composition of the lubricant in the crankcase.

The providing of the data may comprise: providing the data to an engine control device; and the method may further comprise, in response to the received data, the engine control device causing operation of the suction control device. The providing of the data may comprise: providing the data to a control device of the lubricant container; and the method may further comprise, in response to the received data, the control device of the lubricant container causing operation of the suction control device. The providing of the data may comprise: providing the data to a control device of a dock for the lubricant container; and the method may further comprise, in response to the received data, the control device of the dock causing operation of the suction control device. The providing of the data may comprise: providing the data to a control device distributed in control devices selected from a list comprising: an engine control device, a control device of the lubricant container, and/or a control device of a dock for the lubricant container; and the method may further comprise, in response to the received data, the distributed control device causing operation of the suction control device.

The causing of the operation of the suction control device may further comprise controlling the pressure gradient, based on the data, by controlling a device selected from a list comprising: a pump, a throttle, an orifice, and/or a venturi effect system.

The receiving, at the control device, of the signal may comprise receiving the signal at an engine control device and/or at a control device of the lubricant container and/or at a control device of a dock for the lubricant container.

The suction control device may be coupled to the lubricant circulation system associated with the engine. The suction control device may comprise a scavenging pump configured to pump the lubricant out of the crankcase. The suction control device may comprise an electric pump and/or a hydraulic pump and/or a pneumatic pump configured to pump the lubricant into the lubricant container.

The suction control device may be coupled to a vent of the crankcase. The suction control device may comprise a vacuum pump configured to pump gas out of the crankcase. The suction control device may further comprise at least one of a throttle, a controllable orifice and a venturi effect system.

The lubricant container may comprise a replaceable lubricant container comprising a coupling configured to provide fluidic communication between a reservoir of the container for holding the lubricant and the lubricant circulation system associated with the engine.

The providing the data to the control device may comprise providing the data when positioning of the container permits fluidic communication between the reservoir and the fluid circulation system associated with the engine. A data provider of the container may provide the signal and/or the data to the control device when positioning of the container permits fluidic communication between the reservoir and the fluid circulation system associated with the engine.

The provided data may comprise additional data based on at least one property of the lubricant. The at least one property may be selected from the group consisting of: an amount of lubricant, a temperature of the lubricant, a pressure of the lubricant, a viscosity of the lubricant, a viscosity index of the lubricant, a density of the lubricant, an electrical resistance of the lubricant, a dielectric constant of the lubricant, an opacity of the lubricant, and/or a chemical composition of the lubricant.

The provided data may comprise additional data based on at least one property of the engine. The at least one property of the engine may comprise information in connection with at least one of a geographical location of the engine; and/or history of operation of the engine; and/or load of the engine; and/or an abnormal combustion event, such as occurrence of a mega-knock event.

The provided data may comprise additional data based on at least one property of the fuel. The at least one property of the fuel may be selected from the group consisting of: an oxygen concentration of the fuel; at least one characteristic of the distillation of the fuel, a viscosity of the fuel, a density of the fuel, an electrical resistance of the fuel, a dielectric constant of the fuel, an opacity of the fuel, and/or a chemical composition of the fuel.

The method may further comprise sensing the at least one property, and the additional data may be based on the sensed property.

The method may further comprise, in response to the received signal providing the data to a memory. The providing of the data to the memory may comprise storing the data obtained from the control device in the memory. The memory may be distributed in memories selected from a list comprising: a memory of an engine management device, a memory of a data provider of the lubricant container, and/or a memory of a data provider of a dock for the lubricant container.

As already stated, a lower pressure in the crankcase of the engine compared to the pressure in the combustion chamber of the engine reduces the propensity for lubricant to accumulate around the top of the piston ring and the liner, thus inhibiting or reducing the tendency of the lubricant to enter the combustion chamber, and therefore inhibiting or reducing the abnormal combustion events such as pre-ignition events, for example by minimizing a frequency of pre-ignition events.

Therefore, in another aspect of the present disclosure, there is provided a use of a suction control device to maintain a pressure gradient between a combustion chamber and a crankcase of an internal combustion engine to inhibit or reduce entry of lubricant from the crankcase into the combustion chamber. This may enable or facilitate inhibition or reduction of the incidence of abnormal combustion events in the combustion chamber such as pre-ignition leading to mega-knock, such as occurrence of a mega-knock event.

Such a use may provide a simple and inexpensive solution in order to mitigate pre-ignition, particularly in smaller engines with high specific torque (torque per unit engine swept volume) and high power output, operating at low rotational speeds, such as around 1500 revs/min.

In another aspect of the present disclosure, there is provided an apparatus configured to control a pressure gradient between a combustion chamber and a crankcase of an engine, comprising:
  a control device configured to receive a signal indicating that a lubricant container is coupled to a lubricant circulation system associated with the engine,
  wherein the apparatus is further configured to, in response to the received signal, provide data to cause operation of a suction control device for facilitating control of the pressure gradient.

The apparatus may comprise an engine comprising a fluid circulation system adapted for fluidic communication with a reservoir of the lubricant container. The apparatus may further comprise the lubricant container.

The disclosure extends to:
  a computer readable medium comprising program instructions operable to program a processor to perform the method of any aspect of the disclosure, and/or
  a replaceable lubricant container for an engine comprising the computer readable medium of any aspect of the disclosure, and/or
  a control device adapted for use with an apparatus and/or a container of any aspect of the disclosure, and/or
  a vehicle comprising an apparatus or a control device of any aspect of the disclosure.

The disclosure extends to methods and/or apparatus substantially as herein described with reference to the accompanying drawings.

Any feature in one aspect of the disclosure may be applied to other aspects of the disclosure, in any appropriate combination. In particular, features of method aspects may be applied to apparatus aspects, and vice versa.

Figure 4:
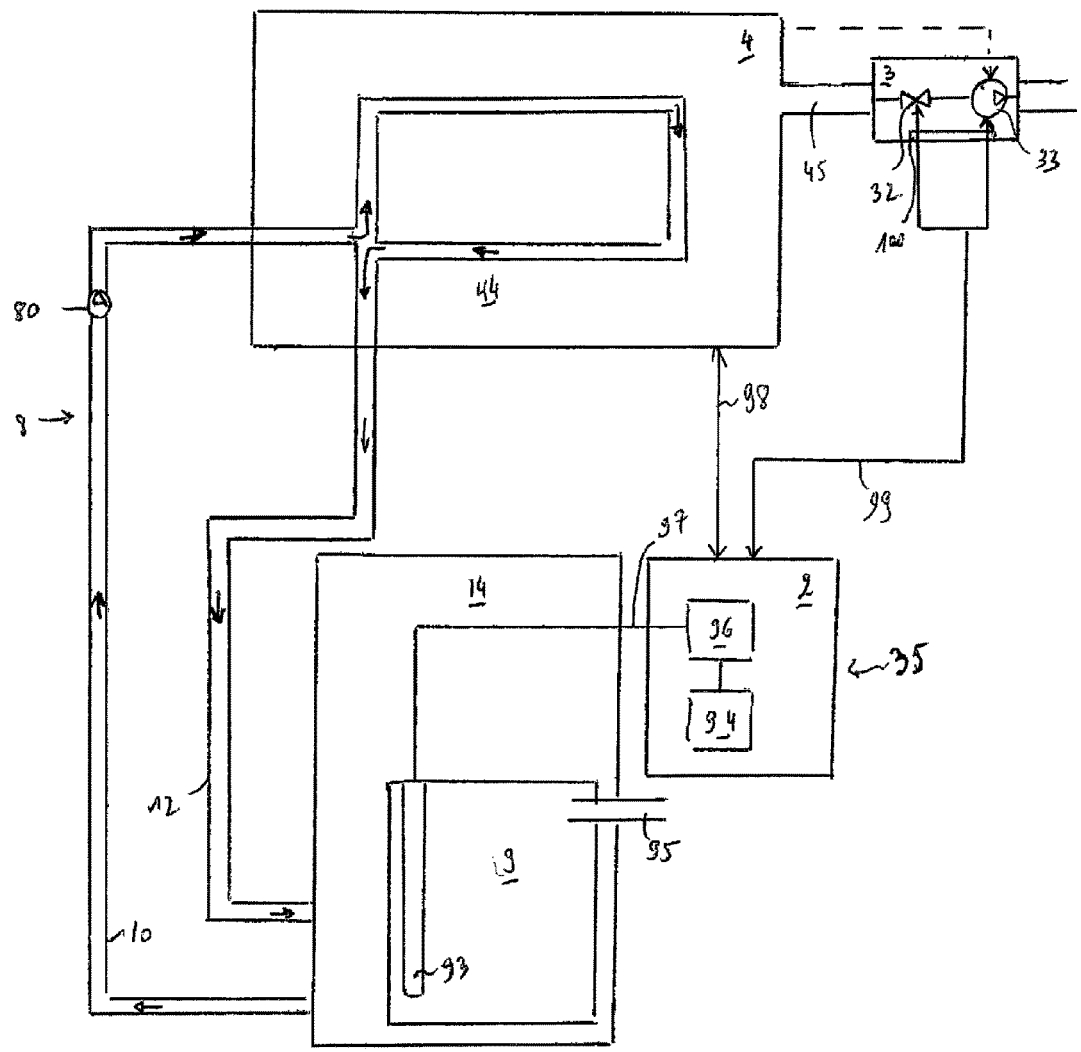
Figure 5:
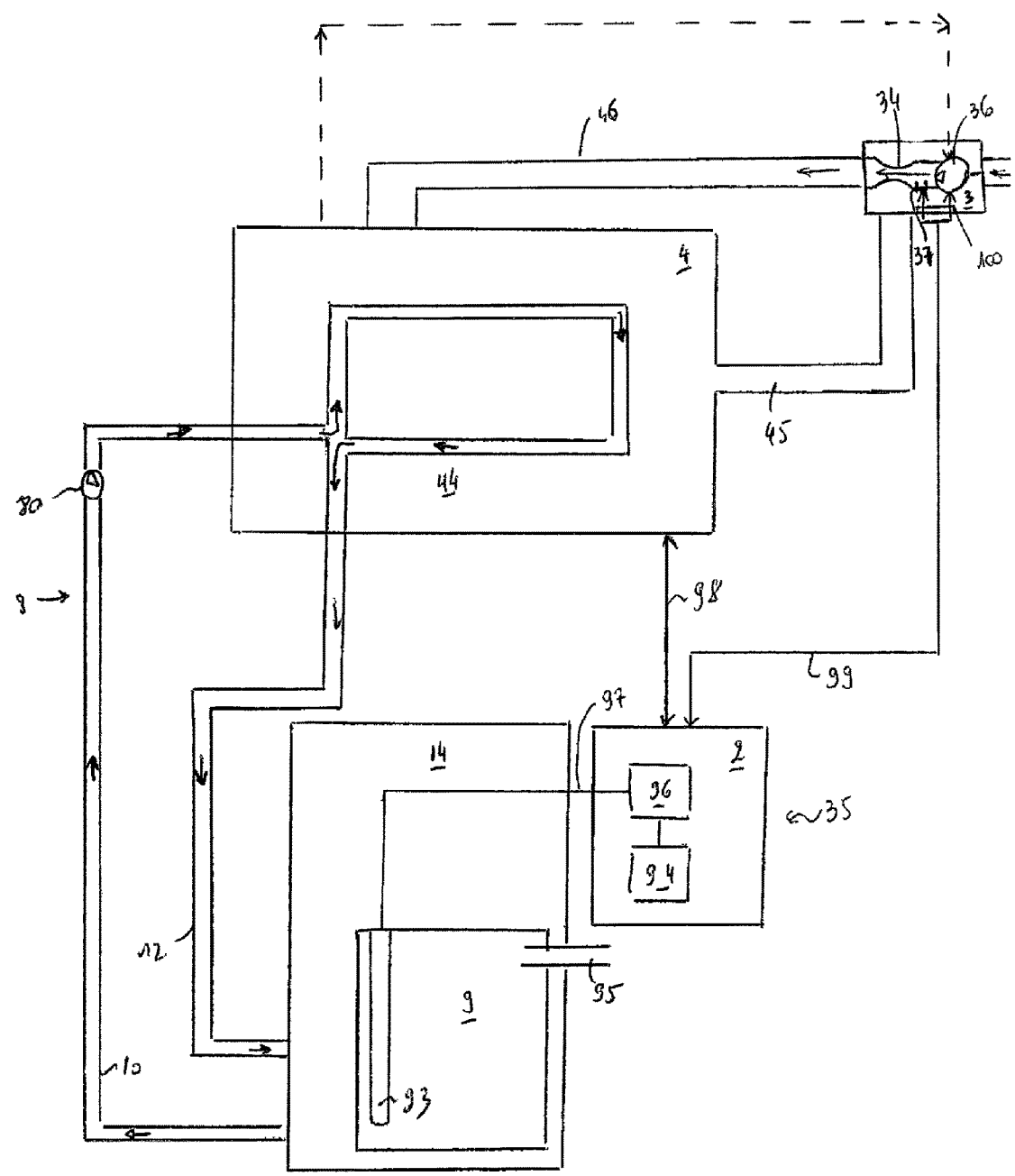
Figure 6:
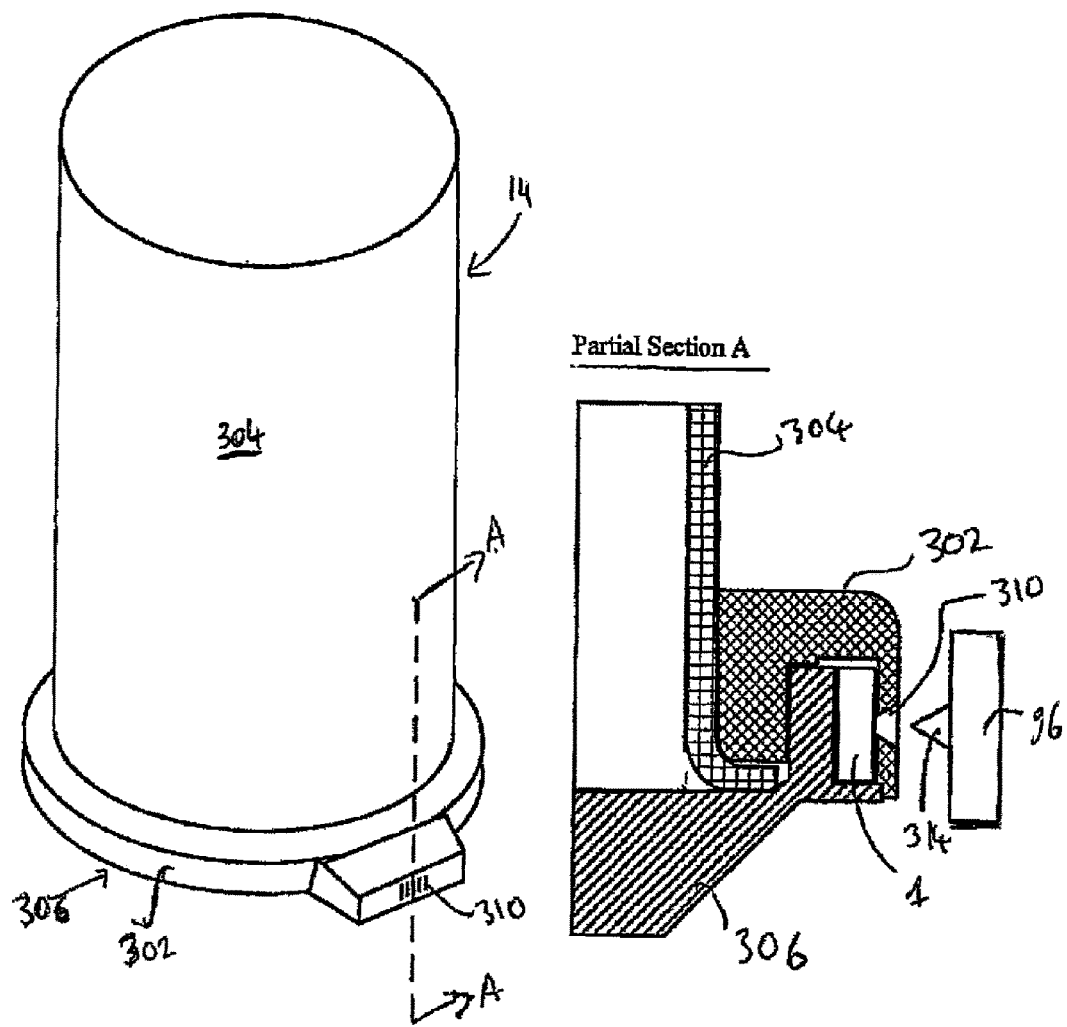

Embodiments will now be described, by way of example only, with reference to the accompanying drawings, in which:

FIG. 1 shows a schematic illustration of a vehicle;

FIGS. 2 to 5 respectively show schematic illustrations of components of the vehicle of FIG. 1; and FIG. 6 shows in schematic elevation view, a replaceable lubricant container for an engine and a partial section through a wall of the container.

In the drawings, like reference numerals are used to indicate like elements.

FIG. 1 shows a vehicle 6 comprising an engine 4 and a lubricant container 14.

The engine 4 comprises an engine block 40, a combustion chamber 41, at least one piston 42, a crankshaft 43, a crankcase 44 housing the crankshaft 43. The engine 4 also comprises a lubricant circulation system 8 associated with the engine 4, where the lubricant may be circulated in the engine and/or may be circulated outside the engine 4.

The lubricant circulation system 8 is adapted to provide lubricant to the bearings and moving parts of the engine 4, such as the crankshaft 43 housed in the crankcase 44. The lubricant circulation system 8 is coupled to receive lubricant from a supply line 10, and to return the lubricant that has circulated in the engine 4 via a lubricant return line 12. The lubricant circulation system 8 may comprise at least one return pump 80 for circulating the lubricant within the system 8.

The lubricant container 14 comprises a reservoir 9 for holding the lubricant.

The vehicle 6 further comprises an apparatus 35 configured to control a pressure gradient between the combustion chamber 41 and the crankcase 44 of the engine 4.

To that effect, the vehicle 6 further comprises a suction control device 3, and the apparatus 35 is further configured to provide data to cause operation of the suction control device 3 for facilitating control of the pressure gradient. In some examples, the apparatus 35 may comprise a control device 2 configured to provide the data.

The operation of the suction control device 3 enables to reduce the pressure in the crankcase 44, below the piston 42, and to maintain a lower pressure in the crankcase 44 compared to the pressure in the combustion chamber 41. In some examples, the absolute pressure in the crankcase 44 may be always between 0.2 bar (absolute) (1 bar=$10^5$ Pa) and 1 bar (absolute).

The inventors have discovered that reduction of the pressure in the crankcase 44 compared to the pressure in the combustion chamber 41 can reduce the accumulation or enables inhibition or decrease of entry (e.g. via infiltration of the lubricant in the combustion chamber 41 through a space between the piston 42 and a corresponding liner of the cylinder of the engine 4) of lubricant in the combustion chamber 41. The fact that entry of lubricant in the combustion chamber 41 is reduced or inhibited reduces the frequency of pre-ignition.

Therefore, maintaining and/or controlling a pressure gradient between the combustion chamber 41 and the crankcase 44, with the pressure in the crankcase 44 being maintained and/or controlled to be lower than the pressure in the combustion chamber 41, enables reduction or inhibition of pre-ignition.

It will be appreciated that the disclosure extends to any use of the suction control device 3 to maintain a pressure gradient between the combustion chamber 41 and the crankcase 44 of the internal combustion engine 4 to reduce the accumulation, inhibit or reduce entry of, lubricant from the crankcase 44 into the combustion chamber 41, in order to mitigate pre-ignition.

As explained in greater detail below, the data provided may be an analog and/or a digital signal to enable operation and/or controlled operation of the suction control device 3. In some examples, the data may be provided to the suction control device 3 and/or the control device 2 and/or to the engine 4 to cause operation and/or controlled operation of the suction control device 3.

As illustrated in the Figures and as explained in greater detail below, the suction control device 3 may comprise at least an element selected from a list comprising: a pump, a throttle, an orifice and/or a venturi effect system.

Figure 2:
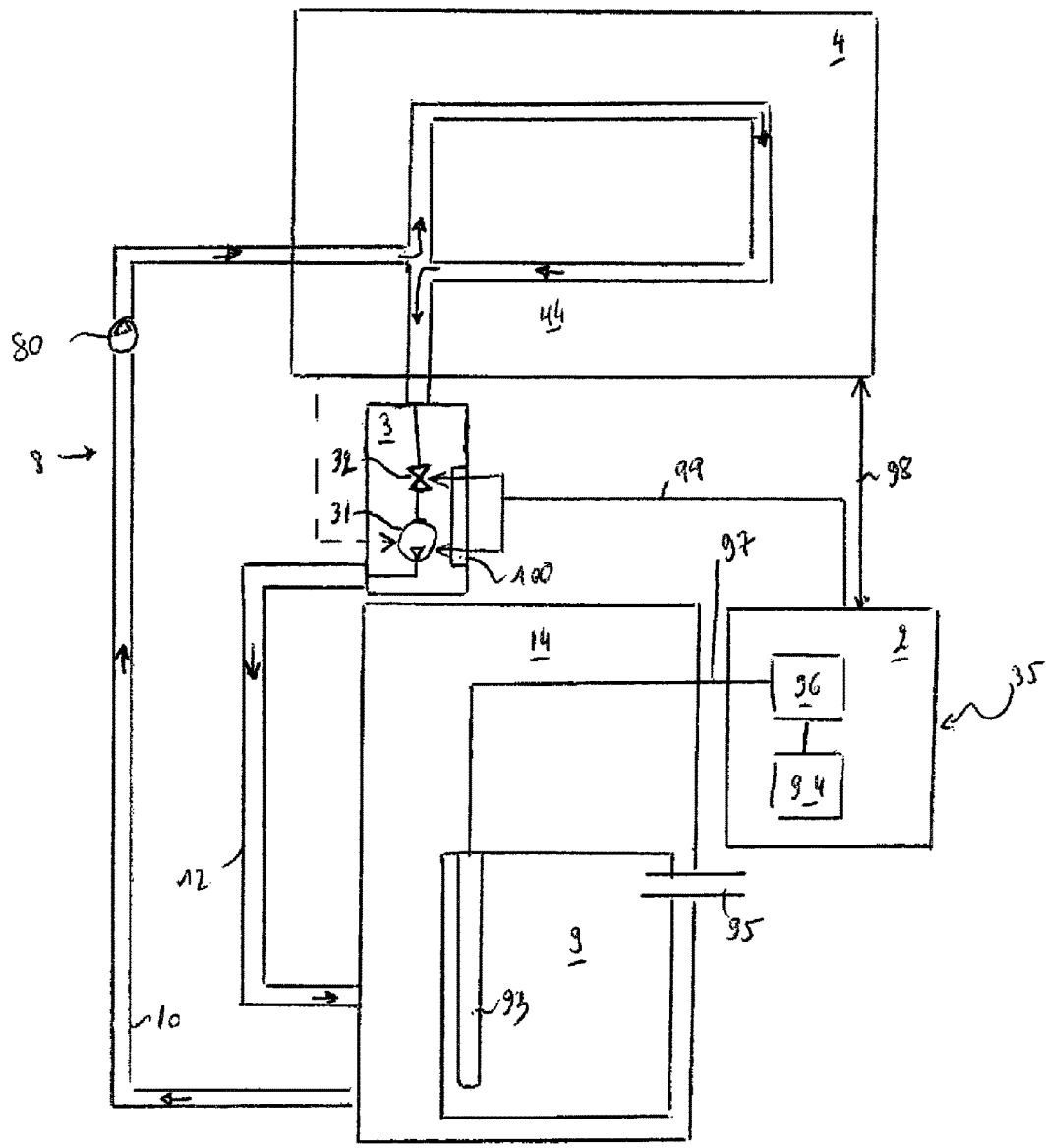
Figure 3:
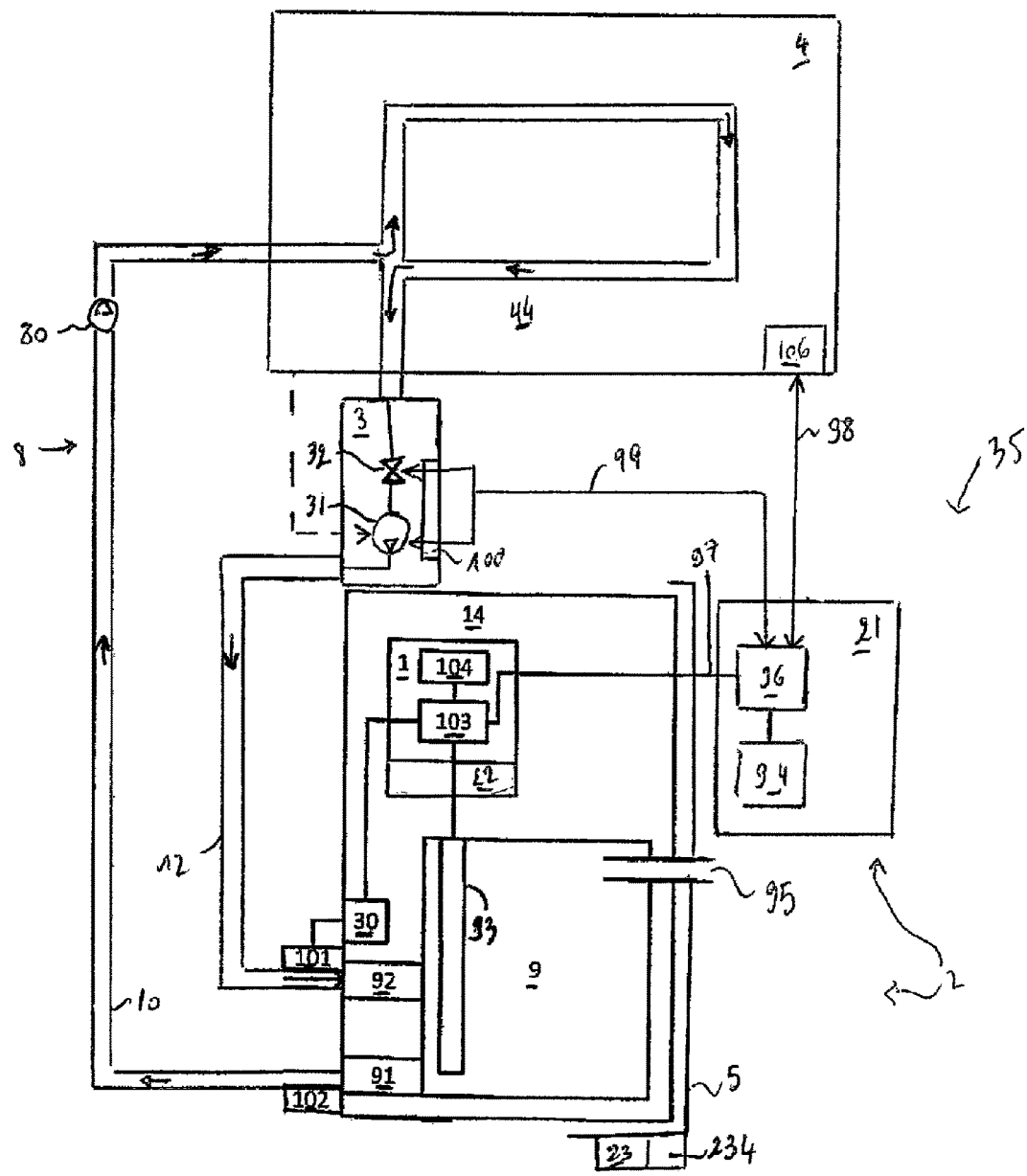

As illustrated in FIG. 2 and in FIG. 3, in some examples the suction control device 3 may be coupled to the lubricant circulation system 8 associated with the engine 4.

In some examples, the suction control device 3 may comprise one or more scavenging pumps 31 configured to pump the lubricant out of the crankcase 44. In some examples, the suction control device 3 may comprise at least one scavenging pump 31 connected to a dry sump of the engine 4, the scavenging pump 31 being configured to drain lubricant by pumping gas from the crankcase 44 to such an extent that the pressure gradient between the combustion chamber 41 and the crankcase 44 of the engine 4 is maintained to inhibit or reduce entry of lubricant from the crankcase 44 into the combustion chamber 41. It will thus be appreciated that in the examples of FIG. 2 and FIG. 3, the one or more scavenging pumps 31 are not used with a view to reduce oil frothing and/or crankshaft windage (drag) in the crankcase 44, although oil frothing and/or crankshaft windage (drag) may also be reduced operating the suction control device 3.

Alternatively or additionally, as illustrated in FIG. 4 and FIG. 5, the suction control device 3 may be coupled to a vent 45 of the crankcase 44.

As illustrated in FIG. 4, in some examples, the suction control device 3 may comprise a vacuum pump 33 configured to pump gas out of the crankcase 44. The vacuum pump 33 is configured to pump gas from the crankcase 44 to such an extent that the pressure gradient between the combustion chamber 41 and the crankcase 44 of the engine 4 is maintained to inhibit or reduce entry of lubricant from the crankcase 44 into the combustion chamber 41.

As illustrated in FIG. 5, in some examples, the suction control device 3 is coupled to the vent 45 of the crankcase 44 and may comprise a pump 36 configured to create a stream of fluid in a venturi effect system 34. The drop of pressure created by the venturi effect system 34 pumps gas out of the crankcase 44 to such an extent that the pressure gradient between the combustion chamber 41 and the crankcase 44 of the engine 4 is maintained to inhibit or reduce entry of lubricant from the crankcase 44 into the combustion chamber 41. As illustrated in FIG. 5, in some examples, the venturi effect system 34 may be coupled to the air inlet 46 of the engine 4. In some other examples, the venturi effect system 34 may be coupled to a liquid duct, such as a water circulation system of the vehicle 6.

In some examples, the one or more scavenging pumps 31 and/or the one or more the vacuum pump 33 and/or the one or more pumps 36 may comprise one or more mechanical pumps. Alternatively or additionally, the one or more scavenging pumps 31 and/or the one or more the vacuum pump 33 and/or the one or more pumps 36 may comprise one or more electric and/or hydraulic and/or pneumatic pumps.

As illustrated by the dotted arrow in the Figures, in some examples, the suction control device 3 (e.g., comprising the one or more scavenging pumps 31 and/or the one or more the vacuum pump 33 and/or the one or more pumps 36) may be mechanically driven by the engine 4 and/or power-supplied by the operation of the engine 4 (such as by using the rotation of the engine).

Alternatively or additionally, as illustrated in FIG. 1, the vehicle 6 may comprise a sensor 7 configured to sense at least one property of the crankcase 44 of the engine 4. The property of the crankcase 44 may be at least one property selected from the group consisting of:

a pressure in the crankcase 44,
a temperature in the crankcase 44,
an amount of lubricant in the crankcase 44,
a viscosity of the lubricant in the crankcase 44,
a density of the lubricant in the crankcase 44, and/or
a chemical composition of the lubricant in the crankcase 44.

In some examples, as illustrated in FIGS. 1 to 5, the data provided, e.g., by the control device 2, in order to cause operation of the suction control device 3 may be based on the sensed property.

It will thus be appreciated that the provided data may enable control of the pressure gradient, based on the data, by causing controlled operation of the suction control device 3.

As illustrated in the FIGS. 2 to 5, the suction control device 3 may comprise at least one of a pump (such as the one or more scavenging pumps 31 and/or the one or more the vacuum pump 33 and/or the one or more pumps 36 already described) and/or a throttle 32, a venturi effect system (such as the venturi effect system 34 already described) and/or a controllable orifice 37. Thus controlled operation of the suction control device 3 may be obtained by controlling the operation of the pump 31, 33 and/or 36, and/or the throttle 32 and/or the venturi effect system 34 already described and/or the controllable orifice 37.

As illustrated in FIG. 2, the lubricant container 14 may be a fixed part of the lubricant circulation system 8. Alternatively or additionally, as illustrated in FIG. 3, the lubricant container 14 may comprise a replaceable container comprising a coupling configured to provide fluidic communication between the reservoir 9 of the container 14, for holding the lubricant, and the lubricant circulation system 8 associated with the engine 4. The replaceable container 14 may be received in a dock 5. The replaceable container 14 is described in more detail below.

The disclosure may be applied to the apparatus 35 comprising the control device 2, the control device being further configured to receive a signal indicating that the lubricant container 14 is coupled to the lubricant circulation system 8 associated with the engine 4.

In some examples, in response to the received signal, the apparatus 35 may provide the data to cause operation of the suction control device 3 for facilitating control of the pressure gradient, as already explained.

In the example of FIG. 3, the control device 2 comprises an engine control device 21 and the signal is received at the engine control device 21.

Alternatively or additionally, in some examples, the control device 2 comprises a control device 22 of the lubricant container 14 and the signal may be received at the control device 22 of the lubricant container 14.

Alternatively or additionally, in some examples, the control device 2 comprises a control device 23 of the dock 5 for the lubricant container 14 and the signal may be received at the control device 23 of the dock 5 for the lubricant container 14.

Alternatively or additionally, in some examples, the control device 2 may be distributed in control devices selected from a list comprising: the engine control device 21, the control device 22 of the lubricant container 14 and/or the control device 23 of the dock 5 for the lubricant container 14. The signal may be received at the distributed control device 2.

As illustrated in FIG. 3, the container 14 may further comprise a data provider 1 configured to provide the signal to the control device 2 when positioning of the container 14 permits fluidic communication between the reservoir 9 and the lubricant circulation system 8 associated with the engine 4.

As already explained above, the data provided by the apparatus 35 may be an analog and/or a digital signal to enable operation and/or controlled operation of the suction control device 3.

As illustrated in FIG. 1, the data may be provided by the control device 2 of the apparatus 35 to the suction control device 3 and/or to the engine 4 to cause operation and/or controlled operation of the suction control device 3.

Alternatively or additionally, in some examples, the data may be provided to the control device 2 to cause operation and/or controlled operation of the suction control device 3.

As illustrated in FIG. 3, in some examples, the control device 2 comprises the engine control device 21, and the engine control device 21 is configured to cause, in some examples in response to the received data, operation and/or controlled operation of the suction control device 3. In the example of FIG. 3, the data may be provided when positioning of the container 14 permits fluidic communication between the reservoir 9 and the lubricant circulation system 8 associated with the engine 4. Alternatively or additionally, in some examples, the control device 2 comprises the control device 22 of the lubricant container 14, and the control device 22 of the lubricant container 14 is configured to cause, in some example in response to the received data, operation of the suction control device 3. Alternatively or additionally, in some examples, the control device 2 comprises the control device 23 of the dock 5 for the lubricant container 14, and the control device 23 of the dock 5 is configured to cause, in some examples in response to the received data, operation and/or controlled operation of the suction control device 3. Alternatively or additionally, in some examples, the control device 2 comprises a control device distributed in control devices selected from a list comprising: the engine control device 21, the control device 22 of the lubricant container 14, and/or the control device 23 of the dock 5 for the lubricant container 14. In examples, the distributed control device is configured to cause operation and/or controlled operation of the suction control device 3, in some examples in response to the received data.

In some examples, the provided data comprises additional data based on at least one property of the lubricant in the container 14. In some non-limiting examples, at least one property of the lubricant may be selected from the group consisting of:
  an amount of lubricant (the amount of lubricant includes the absence of the lubricant),
  a temperature of the lubricant,
  a pressure of the lubricant,
  a viscosity of the lubricant,
  a viscosity index of the lubricant,
  a density of the lubricant,
  an electrical resistance of the lubricant,
  a dielectric constant of the lubricant,
  an opacity of the lubricant,
  a chemical composition of the lubricant, and/or
  a grade of the lubricant.

Alternatively or additionally, the provided data may comprise additional data based on at least one property of the engine.

In some examples, the at least one property of the engine comprises information in connection with a geographical location. It may be that the additional information comprises information in connection with the fact that the engine is being operated (for example in a vehicle) in a geographical area where abnormal combustion problems are common. For example, if the engine is intended to be operated in a geographical area where the fuel quality and/or the conditions of operations are known to exacerbate abnormal combustion, the additional information may cause operation and/or control operation of the suction control device 3 such that the pressure in the crankcase 44 is reduced more than in other geographical areas where the fuel quality and/or the conditions of operations are different. For example, the additional data may comprise information indicating operation of the engine in an area where the fuel is known to exacerbate abnormal combustion and thus causing a lower crankcase pressure.

Alternatively or additionally, the property of the engine may comprise information in connection with history of operation of the engine. In some non-limiting examples, history of operation may include information such as mileage of the engine and/or of the vehicle and/or with such as repair and/or maintenance operations for the vehicle and/or engine such as e.g., replacing the lubricant, etc.

Alternatively or additionally, the at least one property of the engine may comprise information in connection with load of the engine. The apparatus 35 may thus provide data to cause operation and/or controlled operation of the suction control device 3, based on the additional data based on the load of the engine. The additional data mays thus enable, at a given speed of the engine, the suction control device 3 to be operated to cause the pressure to be dropped specifically to mitigate the effects of abnormal combustion at a high engine load.

Alternatively or additionally, the at least one property of the engine may comprise information in connection with an abnormal combustion event, such as occurrence of a mega-knock event. The apparatus 35 may thus provide data to cause operation and/or controlled operation of the suction control device 3, based on the additional data based on the occurrence of a mega-knock event.

Alternatively or additionally, the provided data may comprise additional data based on at least one property of the fuel. In some examples, the at least one property of the fuel may be selected from the group consisting of:

an oxygen concentration of the fuel;
at least one characteristic of the distillation of the fuel,
a viscosity of the fuel,
a density of the fuel,
an electrical resistance of the fuel,
a dielectric constant of the fuel,
an opacity of the fuel, and/or
a chemical composition of the fuel.

It is understood that the at least one property may be sensed, and the additional data may be based on the sensed property.

The at least one property may be sensed by a sensor.

As illustrated in FIGS. 2 to 5, the container 14 may comprise a sensor 93 configured to sense the at least one property of the lubricant in the reservoir 9 of the lubricant container 14. A location sensor may comprise a GPS (Global Positioning System) of the vehicle and/or of the engine.

Alternatively or additionally, the property of the fuel may be sensed by a sensor, for example located in a fuel tank of the vehicle, configured to sense a fuel property, such as for example by measuring a dielectric constant of the fuel. The sensor may be configured to infer oxygen concentration in the fuel. The sensor may also be configured to infer characteristics of the distillation of the fuel so as to cause operation of the suction control device 3 accordingly, in order to reduce abnormal combustion.

It is thus understood that the apparatus may be configured to cause operation and/or controlled operation of the suction control device 3 based on the property of the crankcase 44. However, it is understood that the apparatus may also be configured to cause operation and/or controlled operation of the control suction device 3 based on the additional data, such as a property of the lubricant and/or a property of the engine and/or a property of the fuel.

As illustrated in FIG. 3, the data provider 1 may be configured to further provide the data, for example the data comprising the additional data. In examples the data provider 1 may be coupleable to provide the data to the control device 2, such as the engine control device 21 via a communication link 97. The data provider 1 may be positioned on the container 14 so that, when the container 14 is coupled in fluidic communication with the lubricant circulation system associated with the engine, the data provider 1 is also arranged to communicate the data with the control device 2, and if the container 14 is not positioned for fluidic communication with the lubricant circulation system 8, communication with the data provider 1 is inhibited.

In some examples, the additional data comprises the data about the fluid container 14.

Alternatively or additionally, in some examples, the additional data provided by the data provider 1 may comprise the property of the engine, such as information in connection with a geographical location and/or history of operation and/or load of the engine and/or incidence of abnormal combustion such as mega-knock. For example, the data provider 1 may be configured to provide data that in connection to the fact that the engine is being operated in an area where the fuel and/or the operating conditions may cause pre-ignition.

In some examples, the data, for example the data obtained from the control device 2, may further be provided to a memory. In some examples, the memory may be distributed in memories selected from a list comprising: a memory 94 of a management device (for example comprising the control device 2), a memory 104 of the data provider 1 of the lubricant container 14, and/or a memory 234 of a data provider of the dock 5 for the lubricant container 14.

As illustrated in FIG. 3, in examples the lubricant container 14 may comprise a lubricant outlet port 91 which is coupled to the reservoir 9. The outlet port 91 is coupleable to supply lubricant to the lubricant circulation system 8 associated with the engine 4 via the lubricant supply line 10. The lubricant inlet port 92 is coupleable to the lubricant return line 12 to enable lubricant to circulate from the reservoir 9, around the circulation system 8 associated with the engine 4, and back to the reservoir 9.

The ports 91, 92 of the fluid container 14 comprise couplings, preferably self-sealing, and the container 14 comprises latches 101, 102 configured to secure the container 14 to the fluid supply line 10 and the fluid return line 12. The latches 101, 102 are operable to be released to enable the container 14 to be removed and replaced.

The control device 2, for example the engine control device 21, comprises a processor 96, and the memory 94 configured to store data, for example control data for the suction control device 3 and/or the engine 4.

In examples, the processor 96 may be configured to monitor and/or to control the operation and/or controlled operation of the engine 4 and/or the suction control device 3, via communication links 98 and/or 99, respectively. The processor 96 may be configured to control operation and/or controlled operation of the suction control device 3 based on the monitoring, and based on data read from the memory 94.

The control device 2 may be further configured to obtain the signal indicating that the lubricant container 14 is coupled to the lubricant circulation system 8 associated with the engine 4 and/or the data (for example comprising the additional data) from the data provider 1 via the communication link 97. The control device 2 may be further configured to cause operation of the suction control device 3 and/or the engine 4 based on the data (for example comprising the additional data) obtained from the data provider 1.

The container 14 comprises a vent 95 to enable pressure to be equalised in the reservoir 9 as lubricant is drawn into and out from the reservoir 9.

The container 14 comprises a latch sensor 30 for sensing when the latches 101, 102 are engaged to retain the container 14 in fluid communication with the circulation system 8.

In examples, the sensor 93 may comprise two metallic strips separated from one another on a dip tube of the container 14. The sensor 93 senses the lubricant level in the reservoir 9 based on the capacitance of the strips to provide a signal indicative of the lubricant level to the data provider 1. The sensor 93 may further be configured to sense an electrical resistance of the lubricant thereby to provide an indication of the presence of impurities in the lubricant.

The data provider 1 of the container 14 may comprise a processor 103 arranged to receive signals from the sensor 93 and/or the latch sensor 30. The processor 103 may be arranged to communicate the signal indicating that the lubricant container 14 is coupled to the lubricant circulation system 8 and/or the data (for example comprising the additional data) to the control device 2 via the communication link 97. The processor 103 may be arranged to encode the communicated signal and/or data.

The data provider 1 may further comprise a memory 104 for storing data (for example in an encoded format) describing the at least one property of the lubricant and/or the engine and/or the fuel, as described above. In particular, the memory 104 may store data including at least one of: the grade of lubricant and/or fuel, the type of lubricant and/or fuel, the date on which the fluid was filled or replaced, a unique identifier of the container 14, an indication of whether the container is new, or has previously been refilled or replaced, an indication of the vehicle mileage and/or area of operation, the number of times the container 14 has been refilled or reused, and the total mileage for which the container has been used, etc.

The suction control device 3 may comprise a communication interface 100 arranged to communicate operational parameters of the suction control device 3, such as pump speed and/or throttle position and/or orifice position, to the processor 96 of the control device 2 via the communication link 99. The communication interface 100 may further be operable to receive command from the control device 2 and to modify operation of the suction control device 3 based on the received commands.

The engine 4 may comprise an engine communication interface 106 arranged to communicate operational parameters of the engine 4, such as engine speed and throttle position, to the processor 96 of the control device 2 via the communication link 98. The engine communication interface 106 may further be operable to receive engine command from the control device 2 and to modify operation of the engine 4 based on the received commands.

The memory 94 of the control device 2 comprises non-volatile memory configured to store:
  identifiers of acceptable lubricants and/or fuels for use in the engine 4;
  data defining a first container lubricant level threshold and a second lubricant level threshold;
  data indicative of an expected container lubricant level based on the mileage of the vehicle;
  data defining a service interval, wherein the service interval is the time period between performing maintenance operations for the vehicle such as replacing the lubricant;
  the vehicle mileage;
  sets of engine configuration data and/or intended area of operation of the engine for configuring the engine to operate in a selected way;
  an association (such as a look up table) associating fluid identifiers (such as lubricant and/or fuel) with the sets of engine configuration data; and
  data indicative of an expected lubricant and/or fuel quality based on the mileage of the vehicle and/or the area of operation of the engine and/or vehicle.

The processor 96 is operable to compare data stored in the memory 94 with data obtained from the data provider 1 of the container 14 and/or from the communication interface 100 of the suction control device 3 and/or from the communication interface 106 of the engine 4.

The processor 103 of the container 14 may be configured to obtain data indicating the expected lubricant level based on the mileage since the lubricant was last refilled, and to compare the lubricant level sensed by the sensor 93 with stored data. In the event that this comparison indicates that the lubricant level is changing more quickly than expected, the data provider 1 can be configured to send additional data to the control device 2 to modify a service interval for the vehicle based on this comparison.

The processor 103 of the container 14 may be configured to encode and/or the memory 104 may store additional data comprising information for the control device 2 that the engine is operated in an area where the fuel and/or the conditions of operation of the engine may provoke pre-ignition.

Many different types and grades of lubricant and/or fuel are available and the data provider 1 may comprise an identifier of the lubricant.

The data provider 1 may comprise a computer readable identifier for identifying the lubricant and/or the fuel. The identifier may be an electronic identifier, such as a near field RF communicator, for example a passive or active RFID tag, or an NFC communicator.

The data provider 1 may be configured for one way communication. For example the data provider 1 may be configured only to receive data from the control device 2, so that the data can be provided to the memory 104 at the container 14. For example the memory 104 may be configured to receive data from the engine control device 21. This enables data to be stored at the container 14. Such stored data can then be provided from the memory 104 to diagnostic devices during servicing and/or during replacement of the container 14. Alternatively the data provider 1 may be configured only to provide data to the control device 2. In some possibilities, the data provider 1 is adapted to provide data to and receive data from the control device 2.

The memory 104 is optional. The computer readable identifier may be an optical identifier, such as a barcode, for example a two-dimensional barcode, or a colour coded marker, or optical identifier on the container 14. The computer readable identifier may be provided by a shape or configuration of the container 14. Regardless of how it is provided, the identifier may be encrypted.

The communication links 97, 98 and/or 99 may be any wired or wireless communication link, and may comprise an optical link.

The latches 101, 102, are optional and the container 14 may simply be fluid coupled to the circulation system 8. The container 14 can be secured by gravity, an interference fit, a bayonet coupling, or any appropriate fixture.

The crankcase 44, the container 14 and the fuel tank of the vehicle have been described as comprising particular types of sensors 7 and 30 and 93 respectively. However, any of these sensors may be omitted. Where sensors are used any type of sensor, or combination of sensors can be used. For example, to sense the level of lubricant in the container 14: a mechanical float, a position sensor, an electrical coil, capacitive sensors, resistivity sensors, ultrasonic level detection, visible or infra-red light detection, pressure sensing, or other sensors. The sensor 93 may provide information about the level in a continuous range between two fixed points or as discrete levels (e.g. full, half full, empty). Additionally, if the level of the lubricant increased rapidly it could indicate some form of failure in the engine 4 and provide an early warning mechanism to help prevent further damage to the engine 4. The crankcase 44 and/or the container 14 and/or the fuel tank may comprise sensors configured to sense at least one of a temperature, pressure, viscosity, density, electrical resistance, dielectric constant, opacity, chemical composition or amount of the lubricant and/or fuel. It will further be appreciated that a plurality of lubricant and/or fuel sensors could be provided, each to sense a different property of the lubricant and/or fuel. The latch sensor 30 could be configured to communicate continuously with the container 14 or at selected time intervals or in response to a signal from the processor 96 of the control device 2.

In the context of the present disclosure, those skilled in the art will appreciate that the fluid ports of the container 14 could comprise any suitable coupling for retaining the container 14 in fluid communication with the lubricant circulation system 8. The port couplings could be arranged to be remotely decoupled from the fluid lines 10, 12 to place the container 14 in its uncoupled configuration. It will further be appreciated that the container 14 could comprise an actuator to decouple the fluid container 14 from the circulation system 8.

Although circulated engine oil is described as being returned to the fluid container 14 for recirculation, in the context of the present disclosure, those skilled in the art will appreciate that circulated engine oil could be collected and stored in a container coupled to the engine 4 and, when convenient, emptied from or otherwise removed from the vehicle 6.

FIG. 6 shows an elevation view of a container 14 and a partial section through a wall of the container 14. The container 14 comprises a body 304, and a base 306. The body 304 is secured to the base by a lip 302. The data provider 1 may be carried in the lip 302.

The lip 302 may include a data coupling 310 to enable the data provider 1 to be coupled to the interface 96 for communicating data with the control device (not shown in FIG. 6). The interface 96 may comprise connectors 314 for connecting the interface 96 with the data provider 1 of the container 14.

The base 306 of the container 14 comprises a fluid coupling (not shown in FIG. 6) for coupling lubricant from the reservoir 9 of the container 14 with the circulation system 8 associated with the engine 4. The fluid coupling and the data coupling 310 are arranged so that connecting the fluid coupling in fluidic communication with the circulation system 8 associated with the engine 4 also couples the data provider 1 for data communication with the control device 2 via the interface 96 by seating the connectors 314 of the interface 96 in the data coupling 310 on the container 14.

In some examples, the interface 96 and the connectors 314 may provide electrical connections for up to eight (8) channels which provide, for example measurements for e.g., lubricant temperature, lubricant pressure, lubricant quality, lubricant type, and the level (e.g. amount) of lubricant in the container 14. The connectors 314 may be arranged to provide electrical power to the data provider 1.

Although the example shown in FIG. 6 comprises conductive electrical connections 314 for communicating with the data provider 1, a contactless connection may also be used. For example, inductive or capacitive coupling can be used to provide contactless communication. One example of inductive coupling is provided by RFID, however other near field communications technology may also be used. Such couplings may enable electrical power to be transferred to the data provider 1, and also have the advantage that the data connection does not require any complex mechanical arrangement and the presence of dirt or grease on the couplings 310, 314 is less likely to inhibit communication with the data provider 1.

The container 14 may comprise a power provider such as a battery for providing electrical power to the data provider 1. This may enable the container 14 to be provided with a range of sensors, including sensors for fluid temperature, pressure and electrical conductivity. Where the container 14 comprises a filter sensors may be arranged to sense these parameters of the lubricant as the lubricant flows into the filter, and after the lubricant has flowed through the filter.

The function of the processors 103, 96 may be provided by any appropriate controller, for example by analog and/or digital logic, field programmable gate arrays, FPGA, application specific integrated circuits, ASIC, a digital signal processor, DSP, or by software loaded into a programmable general purpose processor.

Aspects of the disclosure provide computer program products, and tangible non-transitory media storing instructions to program a processor to perform any one or more of the methods described herein.

The fuel may be any type of fuel, such as conventional gasoline, gasoline-ethanol or flexible-fuel alcohol gasoline (such as containing ethanol).

The engine lubricating oil composition may comprise of at least one base stock and at least one engine lubricating oil additive. Suitable base stocks include bio-derived base stocks, mineral oil derived base stocks, synthetic base stocks and semi synthetic base stocks. Suitable engine lubricating oil additives are known in the art. The additives may be organic and/or inorganic compounds. Typically, the engine lubricating oil composition may comprise about 60 to 90% by weight in total of base stocks and about 40 to 10% by weight additives. The engine lubricating oil composition may be a lubricating oil composition for an internal combustion engine. The engine lubricating oil composition may be a mono-viscosity grade or a multi-viscosity grade engine lubricating oil composition. The engine lubricating oil composition may be a single purpose lubricating oil composition or a multi-purpose lubricating oil composition.

Other variations and modifications of the apparatus will be apparent to persons of skill in the art in the context of the present disclosure.

The invention claimed is:

1. A method of controlling a pressure gradient between a combustion chamber and a crankcase of an engine, the method comprising:
   receiving, at a control device, a signal indicating that a lubricant container is coupled to a lubricant circulation system associated with the engine; and
   in response to the received signal, providing data to cause operation of a suction control device for facilitating control of the pressure gradient such that a pressure in the crankcase is maintained lower than a pressure in the combustion chamber.

2. The method of claim 1, wherein the suction control device comprises at least an element selected from a list comprising: a pump, a throttle, an orifice, and a venturi effect system.

3. The method of claim 1, comprising:
   sensing at least one property of the crankcase of the engine, wherein the provided data is based on the sensed property.

4. The method of claim 3, wherein the property of the crankcase is at least one property selected from the group consisting of:
- the pressure in the crankcase,
- a temperature in the crankcase,
- an amount of lubricant in the crankcase,
- a viscosity of the lubricant in the crankcase,
- a density of the lubricant in the crankcase, and
- a chemical composition of the lubricant in the crankcase.

5. The method of claim 1, wherein the providing of the data comprises:
- providing the data to an engine control device; and
- in response to the received data, the engine control device causing operation of the suction control device.

6. The method of claim 1, wherein the providing of the data comprises:
- providing the data to a control device distributed in control devices selected from a list comprising: an engine control device, a control device of the lubricant container, and a control device of a dock for the lubricant container; and
- in response to the received data, the distributed control device causing operation of the suction control device.

7. The method of claim 5, wherein the causing of the operation of the suction control device further comprises controlling the pressure gradient, based on the data, by:
- controlling a device selected from a list comprising: a pump, a throttle, an orifice, and a venturi effect system.

8. The method of claim 1, wherein the providing of the data comprises:
- providing the data to a control device of the lubricant container; and
- in response to the received data, the control device of the lubricant container causing operation of the suction control device.

9. The method of claim 1, wherein the providing of the data comprises:
- providing the data to a control device of a dock for the lubricant container; and
- in response to the received data, the control device of the dock causing operation of the suction control device.

10. The method of claim 1, wherein the receiving, at the control device, of the signal comprises:
- receiving the signal at an engine control device.

11. The method of claim 1, wherein the receiving, at the control device, of the signal comprises:
- receiving the signal at a control device of the lubricant container.

12. The method of claim 1, wherein the receiving, at the control device, of the signal comprises:
- receiving the signal at a control device of a dock for the lubricant container.

13. The method of claim 1, wherein the receiving, at the control device, of the signal comprises:
- receiving the signal at a control device distributed in control devices selected from a list comprising: an engine control device, a control device of the lubricant container, and a control device of a dock for the lubricant container.

14. The method of claim 1, wherein the suction control device is coupled to the lubricant circulation system associated with the engine.

15. The method of claim 14, wherein the suction control device comprises a scavenging pump configured to pump the lubricant out of the crankcase.

16. The method of claim 14, wherein the suction control device comprises an electric pump and/or a hydraulic pump and/or a pneumatic pump configured to pump the lubricant into the lubricant container.

17. The method of claim 14, wherein the suction control device further comprises at least one of a throttle, a controllable orifice, and a venturi effect system.

18. The method of claim 1, wherein the suction control device is coupled to a vent of the crankcase.

19. The method of claim 18, wherein the suction control device comprises a vacuum pump configured to pump gas out of the crankcase.

20. The method of claim 1, wherein the lubricant container comprises a replaceable lubricant container comprising a coupling configured to provide fluidic communication between a reservoir of the container for holding the lubricant and the lubricant circulation system associated with the engine.

21. The method of claim 20, wherein providing the data to the control device comprises:
- providing the data when positioning of the container permits fluidic communication between the reservoir and the fluid circulation system associated with the engine.

22. The method of claim 20, further comprising:
- a data provider of the container providing the signal or the data to the control device when positioning of the container permits fluidic communication between the reservoir and the fluid circulation system associated with the engine.

23. The method of claim 1, wherein the provided data comprises additional data based on at least one property of the lubricant.

24. The method of claim 23, wherein the at least one property is selected from the group consisting of:
- an amount of lubricant,
- a temperature of the lubricant,
- a pressure of the lubricant,
- a viscosity of the lubricant,
- a viscosity index of the lubricant,
- a density of the lubricant,
- an electrical resistance of the lubricant,
- a dielectric constant of the lubricant,
- an opacity of the lubricant, and
- a chemical composition of the lubricant.

25. The method of claim 23, comprising:
- sensing the at least one property, wherein the additional data is based on the sensed property.

26. The method of claim 1, wherein the provided data comprises additional data based on at least one property of the engine.

27. The method of claim 26, wherein the at least one property of the engine comprises information in connection with at least one of:
- a geographical location of the engine;
- history of operation of the engine;
- load of the engine; and
- an abnormal combustion event, such as occurrence of a mega-knock event.

28. The method of claim 1, wherein the provided data comprises additional data based on at least one property of the fuel.

29. The method of claim 28, wherein the at least one property of the fuel is selected from the group consisting of:
- an oxygen concentration of the fuel,
- at least one characteristic of the distillation of the fuel,
- a viscosity of the fuel, a density of the fuel,
an electrical resistance of the fuel,
a dielectric constant of the fuel,
an opacity of the fuel, and
a chemical composition of the fuel.

30. The method of claim 1, further comprising, in response to the received signal:
providing the data to a memory.

31. The method of claim 30, wherein the providing of the data to the memory comprises:
storing the data obtained from the control device in the memory.

32. The method of claim 30, wherein the memory is distributed in memories selected from a list comprising: a memory of an engine management device, a memory of a data provider of the lubricant container, and a memory of a data provider of a dock for the lubricant container.

33. A computer readable medium comprising program instructions operable to program a processor to perform the method of claim 1.

34. A replaceable lubricant container for an engine comprising the computer readable medium of claim 33 and a reservoir for holding a lubricant.

35. The method of claim 1, wherein the lubricant container is replaceable.

36. A method of inhibiting or reducing entry of a lubricant from a crankcase in to a combustion chamber of an internal combustion engine, the method comprising:
maintaining a pressure gradient between the combustion chamber and the crankcase using a suction control device such that a pressure in the crankcase is maintained lower than a pressure in the combustion chamber.

37. The method of claim 36, wherein the suction control device is coupled to a lubricant circulation system adapted to provide lubricant to the crankcase.

38. The method of claim 37, wherein the suction control device comprises a scavenging pump configured to pump the lubricant out of the crankcase.

39. The method of claim 37, wherein the suction control device comprises an electric pump, a hydraulic pump, and a pneumatic pump configured to pump the lubricant into a replaceable lubricant container.

40. The method of claim 36, wherein the suction control device is coupled to a vent of the crankcase.

41. The method of claim 40, wherein the suction control device comprises a vacuum pump configured to pump gas out of the crankcase.

42. The method of claim 36, wherein the suction control device further comprises at least one of a throttle, a controllable orifice, and a venturi effect system.

43. An apparatus configured to control a pressure gradient between a combustion chamber and a crankcase of an engine, comprising:
a control device configured to receive a signal indicating that a lubricant container is coupled to a lubricant circulation system associated with the engine,
wherein the apparatus is further configured to, in response to the received signal, provide data to cause operation of a suction control device for facilitating control of the pressure gradient such that a pressure in the crankcase is maintained lower than a pressure in the combustion chamber.

44. The apparatus of claim 43, comprising an engine comprising a fluid circulation system adapted for fluidic communication with a reservoir of the lubricant container.

45. The apparatus of claim 43, further comprising the lubricant container.

46. A control device adapted for use with the apparatus of claim 43, wherein the control device is configured to control operation of the suction control device for facilitating control of the pressure gradient based on the provided data.

47. A vehicle comprising the apparatus of claim 43.

* * * * *